(12) United States Patent
Boyer

(10) Patent No.: US 7,208,646 B2
(45) Date of Patent: Apr. 24, 2007

(54) SELECTIVE HYDROGENATION OF BUTADIENE

(75) Inventor: Christopher C. Boyer, Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 141 days.

(21) Appl. No.: 10/926,207

(22) Filed: Aug. 25, 2004

(65) Prior Publication Data

US 2005/0256353 A1   Nov. 17, 2005

Related U.S. Application Data

(60) Provisional application No. 60/571,406, filed on May 14, 2004.

(51) Int. Cl.
C07C 5/03 (2006.01)

(52) U.S. Cl. ............... 585/259; 585/260; 585/261; 585/262

(58) Field of Classification Search ......... 585/259, 585/260, 261, 262
See application file for complete search history.

(56) References Cited

U.S. PATENT DOCUMENTS

| | | | |
|---|---|---|---|
| 2,620,314 A | 12/1952 | Hockstra | 252/448 |
| 4,174,355 A | 11/1979 | Patel et al. | 585/843 |
| 4,179,408 A | 12/1979 | Sanchez et al. | 252/448 |
| 4,273,735 A | 6/1981 | Jacques et al. | 264/5 |
| 4,288,640 A * | 9/1981 | Schuster et al. | 568/855 |
| 4,440,956 A | 4/1984 | Couvillion | 585/260 |
| 4,493,906 A | 1/1985 | Couvillion | 502/346 |
| 4,533,779 A | 8/1985 | Boitiaux et al. | 585/259 |
| 4,831,200 A | 5/1989 | Debras et al. | 585/259 |
| 5,028,665 A | 7/1991 | Hucul | 525/339 |
| 5,081,321 A | 1/1992 | Fukuhara et al. | 568/881 |
| 5,110,779 A | 5/1992 | Hucul | 502/185 |
| 5,134,108 A | 7/1992 | Thakur et al. | 502/318 |
| 5,208,405 A * | 5/1993 | Cheung et al. | 585/274 |
| 5,507,956 A | 4/1996 | Bonse et al. | 210/757 |
| 5,510,568 A | 4/1996 | Hearn | 585/834 |
| 5,595,643 A | 1/1997 | Torimoto et al. | 205/634 |
| 5,597,476 A | 1/1997 | Hearn et al. | 208/208 R |
| 5,756,420 A | 5/1998 | Wittenbrink et al. | 502/313 |
| 5,799,877 A | 9/1998 | Gupta et al. | 239/8 |
| 5,807,477 A | 9/1998 | Hearn et al. | 208/238 |
| 5,948,942 A | 9/1999 | Ramirez de Agudelo | 564/490 |
| 5,977,010 A | 11/1999 | Roberts et al. | 502/244 |
| 6,022,823 A | 2/2000 | Augustine et al. | 502/243 |
| 6,153,556 A | 11/2000 | Shima et al. | 502/348 |
| 6,169,218 B1 | 1/2001 | Hearn et al. | 585/260 |
| 6,284,104 B1 | 9/2001 | Maraschino | 202/154 |
| 6,331,657 B1 | 12/2001 | Kaizik et al. | 568/882 |
| 6,407,295 B1 | 6/2002 | Kaizik et al. | 568/883 |
| 6,414,205 B1 | 7/2002 | Stanley et al. | 585/259 |
| 6,417,136 B2 | 7/2002 | Cheung et al. | 502/330 |
| 6,576,588 B2 | 6/2003 | Ryu et al. | 502/331 |
| 6,734,328 B1 | 5/2004 | Ryu | 585/275 |
| 6,774,275 B2 | 8/2004 | Smith, Jr. et al. | 585/731 |

FOREIGN PATENT DOCUMENTS

| | | |
|---|---|---|
| DE | 2109070 | 10/1971 |
| DE | 2412191 | 3/1974 |
| FR | 1253947 | 1/1961 |
| WO | WO 94/04477 A1 | 3/1994 |
| WO | WO 95/15934 A1 | 6/1995 |

OTHER PUBLICATIONS

G. Tosun, A Study of Cocurrent Downflow of Nonfoaming Gas-Liquid Systems in a Packed Bed, Ind. Eng. Chem. Process Des. Dev., 1984, 23, 35-39.
C.N. Satterfield, Trickle Bed Reactors, AIChE Journal, vol. 21, No. 2, Mar. 1975, pp. 209-228.
T.S. Chou, F.L. Worley, Jr., and D. Luss, Transition to Pulsed Flow in Mixed-Phase Cocurrent Downflow through a Fixed Bed, Ind. Eng. Chem., Process Des. Dev., vol. 16, No. 3, 1977, 424-427.
J.R. Blok, J. Varkevisser and A.A.H. Drinkenburg, Transition to Pulsing Flow, Holdup and Pressure Drop in Packed Columns with Cocurrent-Gas-Liquid Downflow, Chemical Engineering Science, vol. 38, No. 5, pp. 687, 1983.
G. Christensen, S.J. McGovern, S. Sundaresan, Cocurrent Downflow of Air and Water in a Two-Dimensional Packed Column, AIChE J Journal, vol. 32, No. 10, 1986, pp. 1677-1689.
J.G. Boelhouwer, Nonsteady Operation of Trickle-Bed Reactors; Hydrodynamics, Mass and Heat Transfer, Chapter 2, pp. 23-52, 2001.

* cited by examiner

Primary Examiner—Thuan Dinh Dang
(74) Attorney, Agent, or Firm—Kenneth H. Johnson

(57) ABSTRACT

A process for the selective hydrogenation of dienes in mixed streams of olefin containing hydrocarbons, such as butadiene in a mixed $C_4$ stream with minimum loss of monoolefins is disclosed wherein the reactor is operated at conditions which induce pulse flow. The pulse flow is induced in a downflow boiling point reactor by vaporization of a portion of the liquid feed at proper conditions.

10 Claims, 3 Drawing Sheets

US 7,208,646 B2

SELECTIVE HYDROGENATION OF BUTADIENE

This application claims the benefit of provisional application No. 60/571,406 filed May 14, 2004.

BACKGROUND OF THE INVENTION

1. Field of the Invention

The present invention relates to the selective hydrogenation of dienes in mixed streams of olefin containing hydrocarbons, such as butadiene in a mixed $C_4$ stream with minimum loss of monoolefins. More particularly the invention relates to hydrogenation of butadiene in multi-phase reactions where a hydraulic regime is utilized, which provides pulsations, to yield greater mixing and associated interfacial mass transfer and heat transfer. By obtaining a desired vapor and liquid mass flux in a downflow reactor process, fluid pulsations can be induced. Most particularly the invention relates to butadiene hydrogenation with minimum olefin loss in a downflow, boiling point, vapor induced pulse reactor.

2. Related Information

The pulse flow regime has been studied in regard to trickle-bed reactors. Generally, "trickle-bed reactor" refers to a solid particulate packed bed downflow reactor operating in the trickle flow or gas continuous regime. A hydraulic map called a Baker plot is often used to indicate the mass fluxes required to obtain a given hydraulic regime (i.e., trickle, pulse, bubble flow). Weekman, V. W., Jr., and J. E. Myers, "Fluid-Flow characteristics of concurrent gas-liquid flow in packed beds", AIChE Journal, 10, 951 (1964) provides a map of the various hydraulic regimes found in packed beds. These pulses yield turbulent mixing within the reactor system and provide a higher level of mass and heat transfer, not typical of commercial reactors which tend to operate in the hydraulic region known as trickle flow.

Pulse flow in a mixed phase reactor is defined as a hydraulic region in which waves of liquid continuous slugs of material move down the reactor. In between each wave is a region of flow which is considered to be gas continuous. The pulses are discrete bands of material with higher overall density than that of the material both in front and behind the pulse or wave. By changing the overall liquid and vapor mass fluxes within this hydraulic region, the frequency at which the pulses flow down the reactor can be manipulated. Higher overall mass flux yields higher frequency pulses, and lower mass flux yields lower frequency pulses. The mechanism for development of this type of flow is not due to oscillations provided by some type of mechanical device, rather it is a known two-phase (vapor/liquid) hydraulic region which is a function of the relative vapor and liquid velocities.

Fukushima, S. and Kusaka, K., *J. of Chem. Eng. Japan* 10, p. 468 (1977) provided Equations 1 and 2, which demonstrate the increase in mass transfer as one moves into the pulse flow regime. The difference between the liquid to gas mass transfer coefficient for trickle flow and pulsing flow can be seen from the following two equations where equation (1) is for trickle flow and equation (2) is for pulsing flow:

$$k_L a_i = 2.05 S_p^{0.2} Re_l^{0.73} Re_G^{0.2} Sc^{0.5} (dp/D)^{0.2} (1-h_{ext}) D_{ml} / dp^2 \quad (1)$$

$$k_L a_i = 0.11 Re_l Re_G^{0.4} Sc^{0.5} (dp/D)^{-0.3} (1-h_{ext}) D_{ml}/dp^2 \quad (2)$$

where:
- $k_L$ is the mass transfer coefficient
- $a_i$ is the specific interfacial surface area
- $S_p$ is the external surface of particle divided by the square of the particle diameter
- $Re_l$ is the modified Reynolds number of the liquid (density removed)
- $Re_G$ is the modified Reynolds number of the gas (density removed)
- Sc is Schmidt number (ratio of the momentum diffusivity to the mass diffusivity
- dp is the particle diameter,
- D is the diameter of the reactor,
- $h_{ext}$ is the liquid hold up (ratio of the volume of liquid held up in the reactor over the total reactor volume), and
- $D_{ml}$ is the molecular diffusivity of the gas This is presented graphically in FIG. 1 where the ratio of pulse flow mass transfer coefficient to trickle bed mass transfer coefficient is shown to increase with the Reynolds number of the liquid or gas. The Reynolds number of either the liquid or gas is directly proportional to the flow rate, all other variables (diameter of reactor, density and viscosity of component) being constant.

Schuster et al U.S. Pat. No. 4,288,640 identifies a narrow region within the Baker plot where heat transfer benefit occurs as one increases the mass fluxes of the gas and liquid and approaches pulse flow. This region of operation is called transitional flow. Transitional flow represents a narrow region of mass fluxes between trickle flow and pulse flow. This region is essentially on the transition line of the flow map separating pulse flow from trickle flow, which lies at a point where a small change in liquid flow causes a relatively large change in differential pressure drop across the bed. Schuster et al list a range of $\Delta P/L$ of twice the $\Delta P/L$ obtained during trickle bed operation and characterizes the pulse region as one where fluctuations in the pressure difference across the reactor occur and the pressure fluctuations as having the same frequency as the pulses. It is known, however, that the pulse regime extends far beyond the differential pressure drop change of twice trickle flow.

A plot of gas vs. liquid mass flux for pilot and commercial scale reactors was presented in "Trickle Bed Reactors", Charles Satterfield, AIChE Journal, Vol. 21, No. 2, March 1975, pp. 209–228. The author observed that the operating region for the pilot scale reactors was in trickle regime; whereas, some commercial reactors operated in the pulse region. This suggests that during scale-up to commercial size some commercial reactors were inadvertently designed to operate in the pulse region, since at the time, running in pulse mode was considered to lead to undesirable hydraulic instability and breakup of catalyst particles in the packed bed.

With typical trickle bed reactors, like those used for hydrotreating using a solid catalyst, the main resistance toward the desired hydrogenation includes: 1) mass transfer from the gas phase into the liquid phase, 2) mass transfer from the liquid phase onto and off of the catalyst surface, 3) diffusion into and out of the catalyst pore space, 4) adsorption of the reactants onto the catalyst surface, 5) chemical reaction, and 6) desorption of the products into the pore space.

Although reactor operation in the pulse flow region may provide interesting mass transfer benefits, two main concerns exist. The first addresses fixed bed catalyst life. Due to the high liquid and vapor rates, vibration of the fixed bed may occur causing physical catalyst degradation and abrasion over time. Secondly a problem in scale up from pilot plant units may be encountered. The small size of pilot plant reactors induces wall effects which occlude space for radial pulse dispersion and it is not known whether larger diameter reactors provide an equivalent flow pattern at the same liquid and vapor velocities. It is an advantage of this invention that a multi-phase co-current flow reactor system that operates efficiently in the pulse flow region is provided.

SUMMARY OF THE INVENTION

Briefly the present invention is the selective hydrogenation of dienes in a mixed olefin containing hydrocarbon stream, such as butadiene in a mixed $C_4$ stream while operating the multi-phase downflow reactor containing hydrogenation catalyst under conditions of liquid and vapor flow to induce a pulse flow regime. The process is preferably carried out downflow in a vertically disposed reactor containing catalyst packing which may also include inert materials.

DESCRIPTION OF THE PREFERRED EMBODIMENTS

Figure 1:
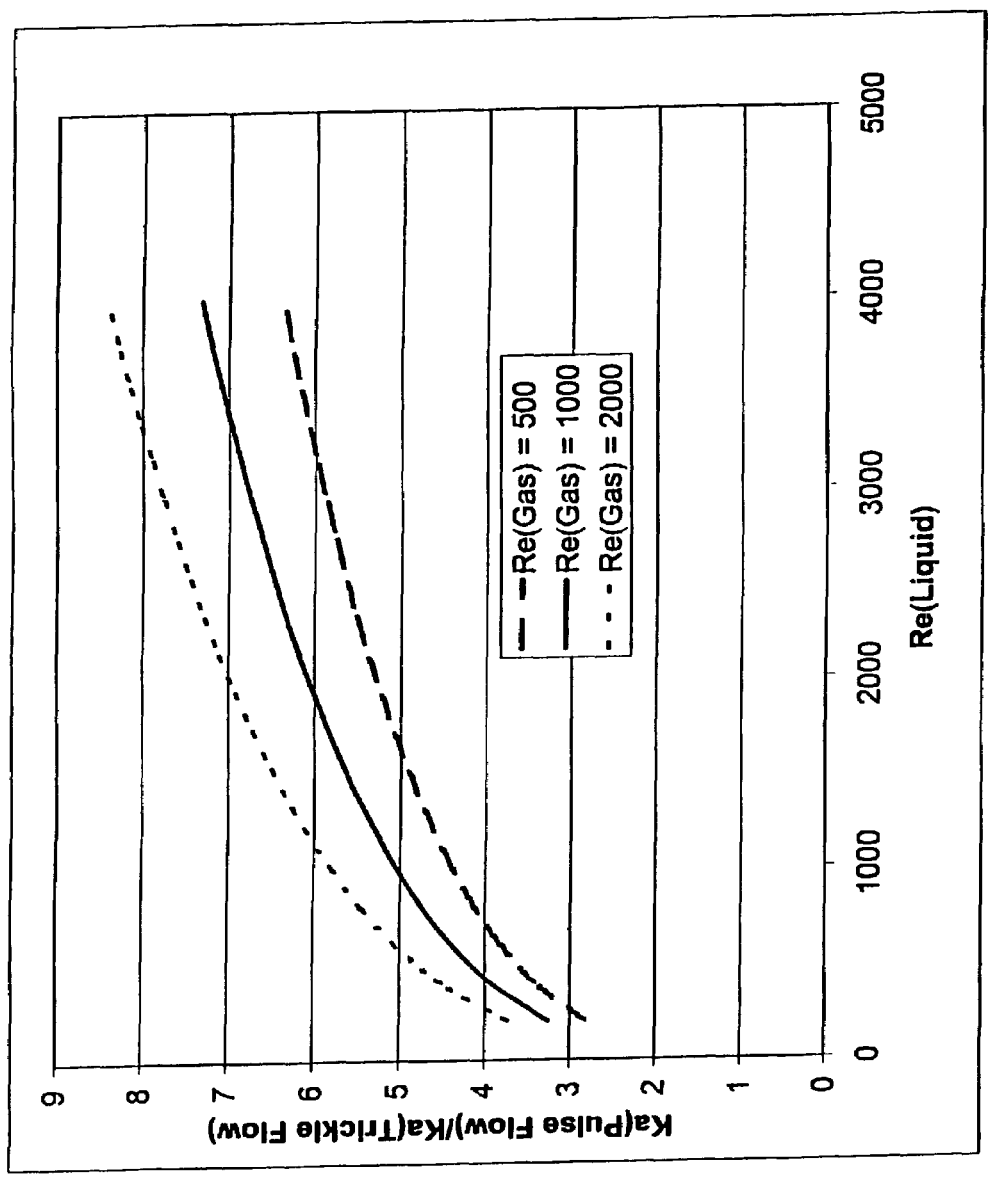
FIG. 1 is a comparison in graphical form of the mass transfer coefficients in pulse flow and trickle flow.
Figure 2:
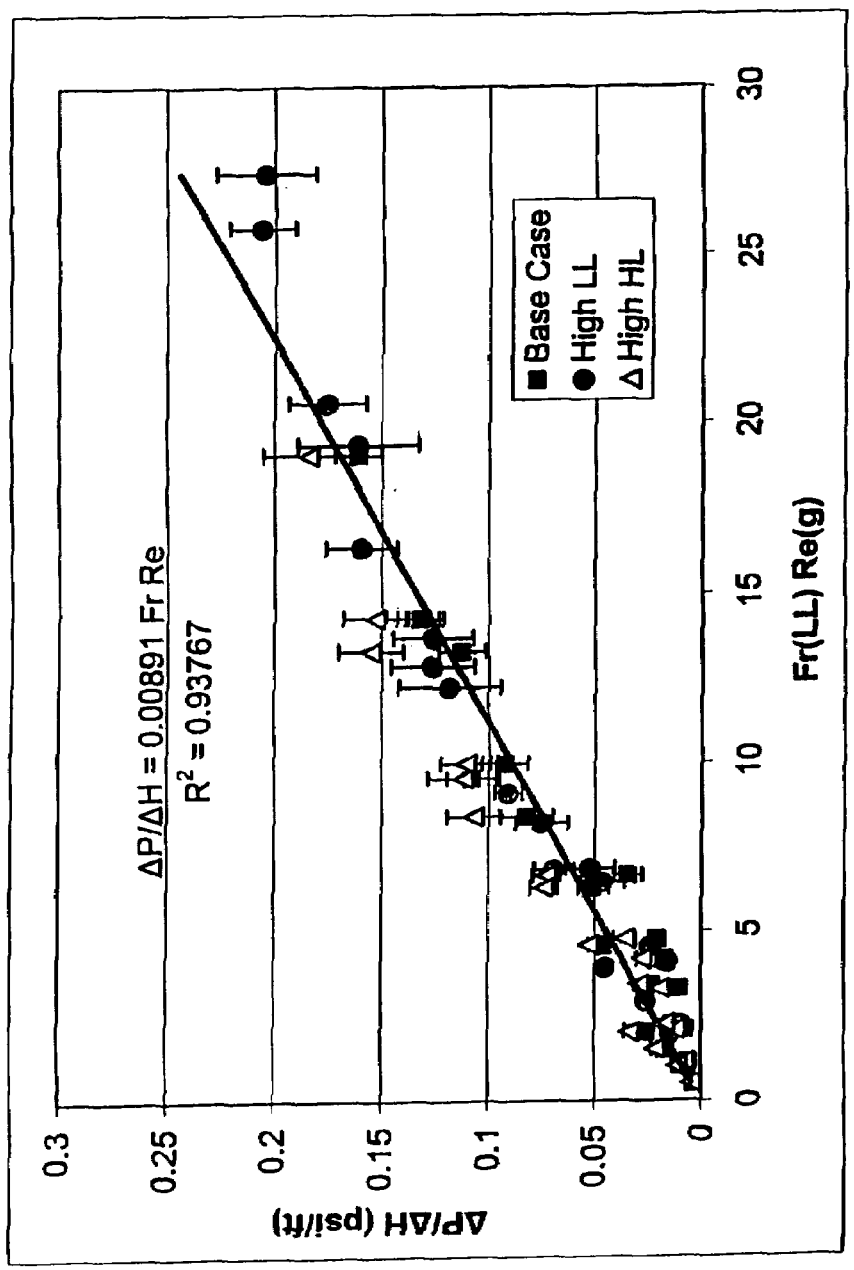
FIG. 2 is a plot of differential pressure versus the product of the Froude Number of the light liquid and the Reynolds Number of the vapor in a packed reactor.
Figure 3:
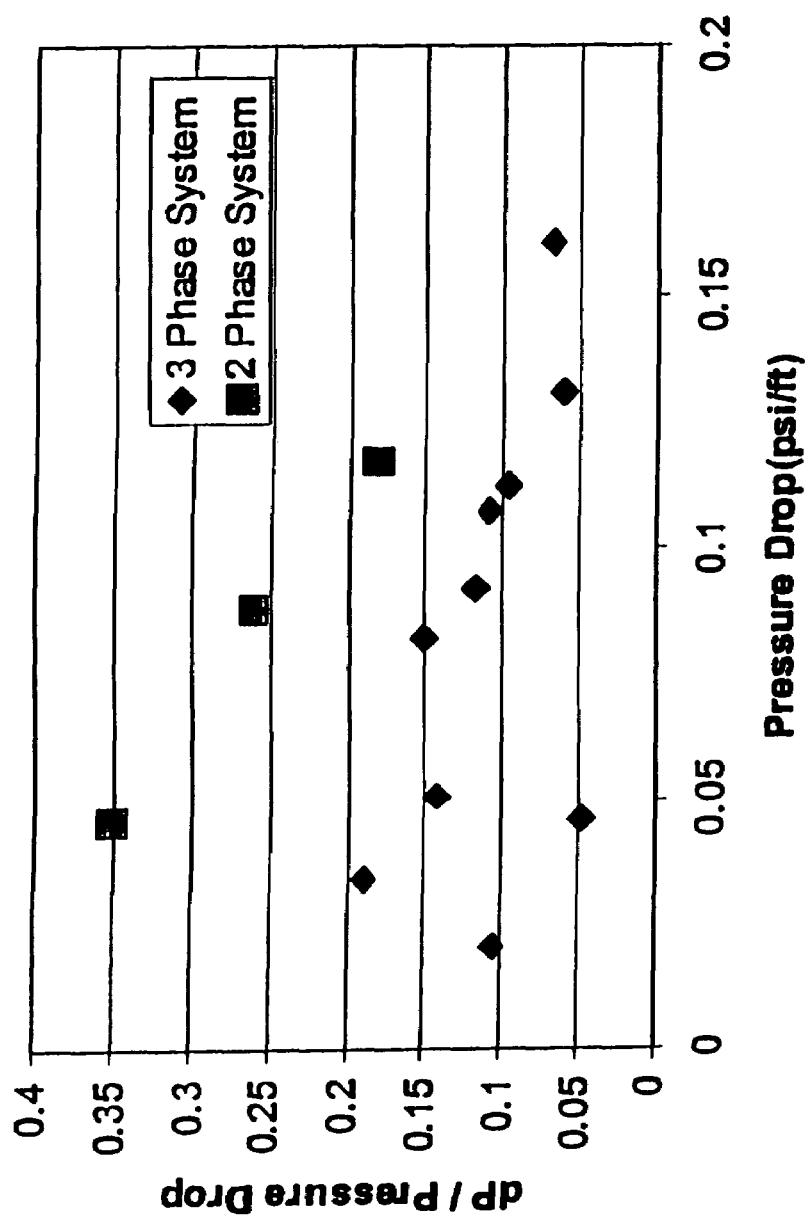
FIG. 3 is a plot of the ratio of the pressure deviations caused by pulse flow to the overall pressure drop versus the overall pressure drop when a three phase (gas/liquid/liquid) system is used.

Suitable mixed streams include $C_4$–$C_7$ hydrocarbon streams. Butadiene is of particular importance because of worldwide excess capacity.

Pulse flow is obtained at high gas and liquid flow rates. The pulses are characterized by large mass and heat transfer rates. Increased catalyst wetting and a continuous mixing between parallel flowing rivulets diminish flow maldistribution. In addition, the formation of local hot spots is reduced, leading to an intrinsically safer process and diminished catalyst deactivation. The pulses continuously mobilize the stagnant liquid holdup to the point where its stagnant nature disappears. Since stagnant holdup represents about 10 to 30 percent of the total liquid holdup in trickle flow operations, its more dynamic character during pulsing flow enhances reactor performance. Axial dispersion is considerably less compared to trickle flow, due to effective radial mixing between the different parallel flowing liquid streams and disappearance of stagnant liquid hold up. Especially undesired consecutive reactions are reduced to lower levels due to better overall plug flow behavior. A further advantage of pulsing flow is much higher radial conductivity. In some cases, depending on the pulse frequency, significant changes in both yield and selectivity occur.

The main benefit with pulse regime reactor operation is that of increased mass transfer and heat transfer due to the associated turbulence produced. When the catalyst physical characteristics are optimized and the reaction kinetics are not limiting, increasing mass transfer is a key to increasing the process performance.

The pulse flow regime may be induced by increasing the gas rate while maintaining the liquid rate until a pressure drop sufficient to induce the pulse flow is achieved. Further the pulsing may be dampened while keeping the mixing characteristics by utilizing a second liquid of different viscosity. The dampening reduces the wear and tear on catalysts and maintains more even flow rates.

A packing positioned within the reactor can be a dispenser affecting the conditions of liquid and vapor flow to induce a pulse flow regime. The bed of catalyst in the reactor may serve as such a packing. A bed of dumped catalyst packing may be particulate material or extrusions of about 0.25 mm to 2 mm or larger. The finer particles provide higher surface area, but also result in a higher pressure drop through the reactor. Thus the catalyst may comprise the packing or the packing may be a separate element from the catalyst.

A detailed description of various disperser packings is described in U.S. Pat. No. 6,774,275 which is incorporated herein. The open space in dumped beds or in structures having fine particles is low, i.e., less than 50 volume % open space. In other embodiments the disperser packing material preferably comprises at least 50 volume % open space up to about 99 volume % open space.

The present process preferably employs a downflow reactor packed with contacting internals or packing material and catalyst through which passes a concurrent multi-phase mixture of hydrocarbon containing the mixed C4s, hydrogen, catalyst and reactants at the boiling point of the system. The system comprises a liquid hydrocarbon phase and a hydrocarbon/hydrogen phase. The pressure is preferentially higher at the top of the reactor than at the bottom.

EXAMPLE

In the present invention butadiene was converted to butylene in a 1" downflow, boiling point reactor operating in the pulse flow regime. Excellent selectivity and activity were achieved. For the present process the exact conditions for pulse flow are unknown. The transition line of the pulse flow regime in a 1" packed column was calculated and plotted for the $C_4/H_2$ system by both the Baker parameters and Froude correlation. A conservative figure would set conditions for pulsing at 29 lb/hr liquid and 10 lb/hr vapor. Assuming a quarter of the $C_4$s will vaporize during the reaction, the liquid flow through the reactor should be set at just above 40 lbs/hr to, achieve pulsing.

The reactor consisted of 2.2 lbs of Kata Luena dispersed Ni catalyst, KL6564 T1.2 (1.3 mm extrudate), dumped into the bottom 10 feet of a 25 foot tall 1 inch diameter reactor. The top 15 feet were filled with ceramic saddles. The catalyst was reduced in hydrogen at 450° F. for 12 hours.

All feed was to the top of the reactor column. Hydrotreated feed was recirculated throughout the process with crude C4 being added to the recycle before it entered the preheater and the reactor column. Hydrogen was added to the top of the reactor. The two-phase bottom effluent was cooled and sent to a degasser vessel where the vapor and a portion of the liquid were removed. Pressure was controlled by the two phase product control valve. Pressure measurements were taken 12.5 feet apart to observe the pressure drop through the bed. The product liquid sample was taken from the bottom of the separator vessel (degasser). The recycle rate was held at ten times the feed rate throughout for most experimental runs so that the butadiene concentration to the reactor inlet was about 6%. The butadiene hydrogenation reaction is exothermic and every mole of butadiene hydrogenated to butylene evaporate seven moles of liquid feed.

The hydrogen rate was kept at about the stoichiometric value for butadiene conversion to butylene which is about 7 standard cubic feet per hour (SCFH) per pound per hour of butadiene feed. The hydrogen partial pressure was calculated by subtracting a calculated hydrocarbon vapor pressure from the total pressure.

The BD (butadiene) index was used and adsorption parameter (K=8) and was calculated as:

$$BDIndex = \frac{WHSV}{p_{H_2}}\left(\frac{1}{K}\ln\left[\frac{W_{BD,in}}{W_{BD,out}}\right] + (W_{BD,in} - W_{BD,out})\right)$$

An unsaturates index was calculated that did not use an adsorption parameter as:

$$UnsatsIndex = \frac{WHSV}{p_{H_2}}\ln\left[\frac{W_{unsats,in}}{W_{unsats,out}}\right]$$

An unsaturates index was also calculated using the adsorption parameter as:

$$UnsatsIndex = \frac{WHSV}{p_{H_2}}\ln\left[\frac{W_{unsats,in}}{W_{unsats,out}}\right](1 + Kw_{BD,lm})$$

The isomerization index was also calculated with and without the adsorption parameter as:

$$IsomIndex = \frac{WHSV}{p_{H_2}}\ln[1 - X_{1c\to 2c}]$$

and $$IsomIndex = \frac{WHSV}{p_{H_2}}[1 - X1c \to 2c](1 = K_{WBD,lm})$$

Where WHSV is the total weight hour space velocity, lbs of feed per hour per pound of catalyst, K is the adsorption parameter, "WBD, in" is the weight fraction of butadiene in the feed, "WBD,out" is the weight fraction of butadiene in the outlet, wt %, "WBD,lm" is the log mean butadiene weight fraction, "Wunsats,in" is the weight fraction of unsaturates in the feed, and "Wunsats, out" is the weight fraction of the unsaturates in the outlet, and X1c→2c is the conversion of 1-butene to 2-butene, wt %.

Table I below contains a typical feed and product composition.

TABLE I

| Component wt. % | Feed | Product |
|---|---|---|
| $C_3$'s | 0.46 | 0.31 |
| 2-methylpropane | 0.80 | 0.75 |
| 2-methylpropene | 1.37 | 1.20 |
| 1-butene | 8.96 | 38.34 |
| 1,3 butadiene | 63.25 | 2.08 |
| n-butane | 15.16 | 16.71 |
| 1-buten-3-yne | 0.99 | 0.00 |
| trans-2-butene | 4.79 | 25.40 |
| 1-butyne | 0.15 | 0.00 |
| methylcyclopropane | 0.02 | 0.02 |
| cis-2-butene | 3.40 | 13.57 |
| 1,2-butadiene | 0.27 | 0.00 |
| $C_5$'s | 0.19 | 0.20 |

Table II below shows the different set of conditions used during the experimental runs.

TABLE II

| Condition | Feed Rate lb/hr | H2/C4 scf/lb | Recycle lb/lb | Pressure psig | Comment |
|---|---|---|---|---|---|
| 1 | 1 | 5 | 10 | 80 | .29 WHSV 40% vaporized 127° F. |
| 2 | 2 | 5 | 10 | 80 | .57 WHSV |
| 3 | 4 | 5 | 10 | 80 | 1.15 WHSV pulse flow |
| 4 | 4 | 5 | 10 | 80 | 28% vaporized |
| 5 | 4 | 5 | 10 | 80 | 59% vaporized |
| 6 | 4 | 5 | 10 | 90 | 134° F. |
| 7 | 4 | 5 | 10 | 60 | 109° F. |
| 8 | 4 | 5 | 10 | 80 | Baseline |

The calculated kinetic indices for all of the reactions were not sensitive to the temperature over the range tested (80–134° F.). The recycling of the butylenes lowers the overall selectivity compared to the per pass selectivity. Hydrogen consumption was high, ~95%. The consumption dropped slightly at lower pressure (60 psig) due to lower kinetics at the lower hydrogen partial pressure. The optimum operating pressure of the column was found to be about 80 psig. At this pressure the hydrogen utilization was high and yet the temperatures were low enough to prevent polymerization of the butadiene and improve catalyst life. The temperature in the bottom section of the column matched the theoretical boiling point curve, indicating that the reactor was boiling.

Kinetic and selectivity improvements were observed by operating at higher flow rates which produced higher differential pressures across the reactor. The reaction kinetics for butadiene saturation was improved by increasing the flow until a 0.5 psi/ft pressure drop was achieved (pulse flow), higher flow gave no further benefit, in the reactor and packing used in the example. The higher the flow rate, and higher the differential pressure, the higher the kinetic rate for butadiene hydrogenation and isomerization. The butadiene concentration was low, so mass transfer limitations were expected.

When compared to a standard butadiene hydrogenation in a distillation column reactor the downflow, boiling point, vapor induced pulse flow reactor the selectivity of the butadiene hydrogenation was much higher.

The invention claimed is:

1. A process for the selective hydrogenation of butadiene in a mixed olefin containing hydrocarbon stream comprising (a) feeding hydrogen and said mixed olefin containing hydrocarbon stream downflow through a reactor containing a bed of hydrogenation catalyst under conditions of liquid and vapor flow to induce a pulse flow regime within the reactor whereby stagnant liquid holdup is not present and (b) hydrogenating said butadiene.

2. The process according to claim 1 wherein the pulse flow regime is induced by increasing the gas rate while maintaining the liquid rate until a pressure drop sufficient to induce pulse flow is achieved.

3. The process according to claim 1 wherein the mixed olefin containing hydrocarbon stream comprises $C_4$–$C_7$ hydrocarbons.

4. The process according to claim 1 wherein a packing is present in said reactor.

5. The process according to claim 4 wherein said packing comprises said hydrogenation catalyst.

6. A process for the selective hydrogenation of butadiene in a mixed $C_4$ stream comprising (a) feeding hydrogen and said mixed $C_4$ stream downflow through a reactor containing a bed of hydrogenation catalyst under conditions of liquid and vapor flow to induce a pulse flow regime within the reactor whereby stagnant liquid holdup is not present and (b) hydrogenating said butadiene.

7. The process according to claim 6 wherein the conditions comprise a temperature and pressure such that the mixture inside the reactor is boiling to such a degree so as to generate enough vapor to induce pulse flow conditions.

8. The process according to claim 6 wherein about 25 weight percent of the liquid feed to the reactor is vaporized in the reactor.

9. The process according to claim 6 wherein the hydrogen feed to the reactor is about the stoichiometric value for butadiene hydrogenation to butylenes.

10. A process for the selective hydrogenation of butadiene in a mixed $C_4$ stream comprising (a) feeding said mixed $C_4$ stream downflow through a reactor containing a bed of hydrogenation catalyst at a weight hourly space velocity of between 0.25 and 1.2 pounds of liquid feed per pound of catalyst, a temperature of between 80° F. and 140° F. and a pressure of between 60 and 90 psig such that about 25 weight percent of the liquid feed is vaporized to induce pulse flow conditions in said reactor whereby stagnant liquid holdup is not present and (b) hydrogenating said butadiene.

* * * * *

UNITED STATES PATENT AND TRADEMARK OFFICE
Certificate

Patent No. 7,208,646 B2                                                     Patented: April 24, 2007

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Christopher C. Boyer, Houston, TX (US); Lawrence A. Smith, Jr., Pasadena, TX (US); William M. Cross, Seabrook, TX (US); and Arvids Judzis, Jr., Houston, TX (US).

Signed and Sealed this Seventeenth Day of July 2012.

In Suk Bullock
Supervisory Patent Examiner
Art Unit 1772
Technology Center 1700